(12) United States Patent
Weippert

(10) Patent No.: US 8,647,878 B2
(45) Date of Patent: Feb. 11, 2014

(54) HIGHLY REFRACTIVE IMMERSION LIQUIDS AND THEIR USE

(75) Inventor: Hans-Joachim Weippert, Aalen (DE)

(73) Assignee: Carl Zeiss AG, Oberkochen (DE)

( * ) Notice: Subject to any disclaimer, the term of this patent is extended or adjusted under 35 U.S.C. 154(b) by 806 days.

(21) Appl. No.: 12/711,978

(22) Filed: Feb. 24, 2010

(65) Prior Publication Data

US 2010/0212547 A1 Aug. 26, 2010

(30) Foreign Application Priority Data

Feb. 25, 2009 (DE) .......................... 10 2009 010 503

(51) Int. Cl.
*C09D 5/00* (2006.01)
(52) U.S. Cl.
USPC ................. 436/18; 560/100; 560/56; 560/17; 106/287.2; 106/287.24; 549/79
(58) Field of Classification Search
USPC .................. 436/18; 560/100, 56, 17; 549/79; 106/287.2, 287.24
See application file for complete search history.

(56) References Cited

U.S. PATENT DOCUMENTS

| 3,437,402 A | 4/1969 | Levins et al. |
| 4,526,711 A | 7/1985 | Sacher et al. |
| 4,689,387 A | 8/1987 | Kajimoto et al. |
| 2008/0135808 A1 | 6/2008 | Kinoshita et al. |

FOREIGN PATENT DOCUMENTS

| DE | 3534527 A1 | 4/1986 |
| DE | 297 24 199 U1 | 6/2000 |
| DE | 10252006 A1 | 5/2004 |
| EP | 0063684 A1 | 11/1982 |
| EP | 0115583 B1 | 8/1984 |
| EP | 0235743 A1 | 9/1987 |

OTHER PUBLICATIONS

Tatsuo Ishiyama et al., "Palladium (0)-Catalyzed Thioboration of Terminal Alkynes with 9-(Alkylthio)-9-borabicyclo [3.3.1]nonane Derivatives: Stereoselective Synthesis of Vinyl Sulfides via the Thioboration-Cross-Coupling Sequence." Journal of American Chemical Society, vol. 115, 1993, pp. 7219-7225.

*Primary Examiner* — Monique Cole
(74) *Attorney, Agent, or Firm* — Fitch, Even, Tabin & Flannery LLP

(57) ABSTRACT

The invention relates to an immersion liquid including at least one compound of the general formula I

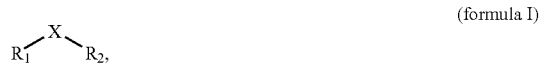

(formula I)

in which $R_1$ and $R_2$ each include at least one ring structure and X denotes: O, S, $NR_3$ with $R_3$ selected from hydrogen or hydrocarbon,

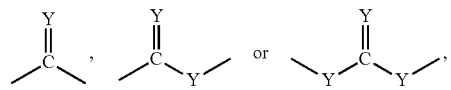

wherein Y denotes independently of each other O, S or $NR_4$ with $R_4$ selected from hydrogen or hydrocarbon. In addition, the invention relates to a further immersion liquid, a compound for an immersion liquid and a use of the immersion liquids or of the compound as an immersion oil for a microscope, in particular for a near-field microscope.

19 Claims, No Drawings

HIGHLY REFRACTIVE IMMERSION LIQUIDS AND THEIR USE

CROSS-REFERENCE TO RELATED APPLICATION

This application claims foreign priority to German Patent Application No. 10 2009 010 503.4, filed Feb. 25, 2009, which is hereby incorporated herein by reference in its entirety.

TECHNICAL FIELD

The invention relates to highly refractive immersion liquids, a highly refractive compound as well as the uses thereof.

PRIOR ART

Light collecting efficiency and resolution in the microscopy are directly dependent on the numerical aperture (NA) of the employed objective. A major problem for example of the single molecule microscopy in living cells is in the autofluorescence of diverse cell components such as for example proteins, cell metabolites and the like. For examining such cells, often, the so-called total internal reflection microscopy (TIRF) is used, which is a wide-field technique. In the total internal reflection fluorescence microscopy, the NA including the refractive indices of immersion oil and cover glass moreover also determines the penetration depth of the excitation light if the illumination is effected through the objective. A particularly large NA then allows illuminating extremely thin layers (below 100 nm).

In order to further increase the NAs of about 1.49 achievable with conventional immersion oil heretofore, for the development of immersion objectives with high NA for the near-field microscopy, compounds or mixtures of compounds with larger refractive index n are necessary. In addition, the compounds are to satisfy various further requirements. Thus, besides the refractive index as high as possible, above all, a low intrinsic fluorescence, a sufficient transmission up to ca. 380 nm, a low volatility as well as a low toxicity are desirable.

From the prior art, various highly refractive compounds and immersion liquids are known. For example, US 2008/0135808 A1 discloses an immersion oil, which is composed of a mixture of diiodomethane and sulfur and has a refractive index n of about 1.78.

In addition, comparable mixtures are already referenced in 1934 by Anderson and Payne (Liquids of High Refractive Index (Nature (1934), Vol. 133, p. 66). From the Handbook of Chemistry and Physics (The Chemical Rubber Co. (1968), Ohio, Robert C. Weast, 49. edition, E-219), among other things, diiodomethane as well as diiodomethane saturated with sulfur are also known as highly refractive immersion liquids.

In proprietary examinations, the following measurement data has been determined to this:
Diiodomethane:
  Refractive index $n_e$ (546.1 nm)=1.7495 (at 20° C.)
  Transmission (d=10 mm) at 420 nm: 4%
  Viscosity (at 20° C.): 9 mm²/s
  Poor glass wetting
Diiodomethane-Sulfur (90:10 Parts by Weight):
  Refractive index $n_e$ (546.1 nm)=1.7896
  Transmission (d=10 mm) at 450 nm: 2%

However, these immersion liquids are insufficient for many applications, since they have a very poor glass wetting, for example. In addition, longer recording times with the so-called "live cell imaging" technique are impossible. However, in particular the "live cell imaging" technique is of particular interest for the modern cell biology, since hereby microscopic fast motion recordings of moving cells can be made. Moreover, the immersion oil is extremely strong-smelling, no longer sufficiently transparent below 450 nm and exhibits high intrinsic fluorescence. This property is a disadvantage in particular in microscopic techniques, which assume single molecule detection in the fluorescence. As an example for such microscopic techniques, the so-called "photo activated localization microscopy (PALM)" technique is to be mentioned, which basically allows a resolution down to 20 nm. With the aid of this technique, by localization of single molecules, which can be determined much more exactly than the conventional assessment limitation, an extremely high-resolution image can be successively formed. In addition, diiodomethane is classified as a compound to be avoided due to its presently unexplained toxicity. Furthermore, diiodomethane has a relatively high volatility despite of a boiling point of about 181° C., whereby the sulfur accumulates in diiodomethane sulfur mixtures and crystallizes from a weight proportion of about 12%. Hereby, continuation of the microscopic examination is complicated or even rendered impossible. Additionally, a high cleaning effort of the concerned apparatus components arises.

PRESENTATION OF THE INVENTION

It is the object of the present invention to provide an immersion liquid, which has a refractive index as high as possible with improved suitability for the microscopy at the same time.

This object is solved by an immersion liquid according to claim 1, an immersion liquid according to claim 14, a compound according to claim 18 as well as a use of the immersion liquid or of the compound according to claim 19. Advantageous configurations with convenient developments are specified in the respective dependent claims, wherein advantageous developments of the immersion liquids are to be considered as advantageous developments of the compound and vice versa.

An immersion liquid according to the invention, which has a refractive index as high as possible with improved suitability for the microscopy at the same time includes at least one compound of the general formula I

(formula I)

in which $R_1$ and $R_2$ each include at least one ring structure and X denotes: O, S, $NR_3$ with $R_3$ selected from hydrogen or hydrocarbon,

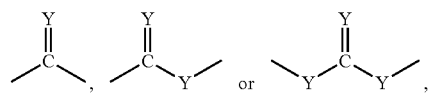

wherein Y denotes independently of each other O, S or $NR_4$ with $R_4$ selected from hydrogen or hydrocarbon. Therein, all of the enantiomers and racemic mixtures of the compound are to be considered as encompassed. Therein, the immersion liquid is in particular suitable for immersion objectives with high NA for microscopes, in particular near-field microscopes, and has a plurality of advantageous characteristics.

Thus, the compound of the general formula I has a high refractive index n, wherein a simple refractive index adaptation—for example to the employed cover glass material—is allowed due to the variable chemical structure of the compound. Therefore, the optical characteristics of the immersion liquid are adaptable to different operating temperatures, for example 23° C. and 37° C., in optimum manner. Moreover, the immersion liquid has a particularly low intrinsic fluorescence F, which is below 10 mg/l quinine sulfate equivalents at an excitation wavelength of 405 nm and a fluorescence emission of 485 nm. Due to the at least two ring structures, the immersion liquid is high-boiling and does not or not to an appreciable extent evaporate at the mentioned operating temperatures. Hereby, on the one hand, it is ensured that refractive index variations will not occur during the application in the microscope, on the other hand, the immission values in the operating range are also substantially reduced. Further advantages are in sufficient wetting of glass surfaces (cover glasses etc.) as well as a high color stability of usual microscopy dyes, since the immersion liquid does not cause any disturbing decoloration of preparations in operations without cover glass.

The compounds designated according to the invention are medium to highly viscous compared to diiodomethane and diiodomethane sulfur mixtures. Thus, the immersion liquid is very well suitable for various microscopic techniques, in particular for the fluorescence microscopy, due to its various advantages. Therein, basically, it can be provided that the immersion liquid includes two or more compounds of the general formula I, thereby providing a particularly simple and precise adaptability of the optical and mechanical characteristics of the immersion liquid to different profiles of requirement.

In an advantageous development of the invention, it is provided that $R_1$— in the general formula I has the general formula II $$R_5\text{—}Z\text{—} \qquad \text{(formula II)}$$

wherein $R_5$ includes the at least one ring structure and Z denotes $(CR_6R_6)_n$, wherein $R_6$ is each independently selected from hydrogen or hydrocarbon and n is an integer between 1 and 10. Hereby, the two ring structures $R_1$ and $R_2$ can be separated from each other by an adjustable spacer (Z), whereby, besides the optical characteristics of the compound of the general formula I, in particular the viscosity and volatility thereof are also specifically modifiable.

In a further advantageous development of the invention, it is provided that the compound of the general formula I has a refractive index n of at least 1.52 and preferably of at least 1.60 at 20° C. in the wavelength range between 435 nm and 645 nm. Preferably, it is provided that the compound of the general formula I has a refractive index $n_D$>1.60, in particular $n_D$>1.64, at 20° C. and 589 nm wavelength. Hereby, the immersion liquid is suitable for immersion objectives with high NA and can be used for microscopic examination of particularly thin layers.

In a further advantageous development of the invention, it is provided that the compound of the general formula I has a transmission of at least 1%, in particular of at least 2%, in the wavelength range between 370 nm and 400 nm, and/or a transmission of at least 15%, in particular of at least 20%, in the wavelength range between 400 nm and 420 nm, and/or a transmission of at least 40%, in particular of at least 50%, in the wavelength range between 420 nm and 450 nm, and/or a transmission of at least 70%, in particular of at least 80%, in the wavelength range between 450 nm and 800 nm, at 20° C. and with a layer thickness of 10 mm.

Further advantages arise by the immersion liquid having a viscosity v of at least 50 mm$^2$/s, in particular of at least 100 mm$^2$/s, in the temperature range between 20° C. and 40° C. In this manner, the immersion liquid has an optimum flowability, in particular for microscopic applications.

In a further advantageous development of the invention, it is provided that the immersion liquid has an Abbe number $V_e$ of at least 18, in particular of at least 20, in the temperature range between 20° C. and 40° C. In this manner, possible image defects are advantageously minimized or at least largely excluded.

In a further advantageous development of the invention, it is provided that $R_1$ and/or $R_2$ of the at least one compound includes at least one monocyclic and/or bicyclic and/or tricyclic ring structure. Hereby, the optical and mechanical characteristics of the compound and thus of the immersion liquid can be adapted to the respective employment purpose in optimum manner. Therein, bi- and tricyclic ring structures in particular have proven to be advantageous for increasing the refractive index.

In further advantageous development, $R_1$ and/or $R_2$ of the at least one compound includes at least one saturated and/or unsaturated and/or aromatic ring structure. Therein, in particular aromatic ring structures have proven to be advantageous for increasing the refractive index.

Further advantages arise if $R_1$ and/or $R_2$ of the at least one compound includes at least one ring structure with at least one heteroatom, in particular O, N and/or S. With the aid of at least one heteroatom or a hetero ring structure, the refractive index of the compound or of the immersion liquid can be advantageously increased.

Therein, in further development, it has proven to be advantageous if $R_1$ and/or $R_2$ of the at least one compound includes at least one further functional group. This too, presents a simple and flexible possibility of adapting the optical, chemical and mechanical characteristics of the immersion liquid to the respective employment purpose in optimum manner.

Therein, it has proven to be advantageous if the at least one further functional group includes a carboxylic acid, a thiocarboxylic acid, a carboxylic acid ester, in particular an alkyl- and/or arylcarboxylic acid ester, a thiocarboxylic acid ester, in particular an alkyl- and/or arylthiocarboxylic acid ester, an ether, in particular an alkyl- and/or arylether, a thioether, in particular an alkyl-/and or arylthioether, a halide, in particular a chloride, bromide and/or iodide, a ketone, a thioketone, an aldehyde, a thioaldehyde, an alcohol, a thiol and/or an amine. Hereby, the refractive index can be optimally adapted to the respective requirements. Therein, in particular sulfur containing functional groups and halides act in refractive index increasing manner.

In a further development of the invention, it has proven to be advantageous if the immersion liquid includes at least one additive, by means of which the viscosity v and/or the refractive index n of the immersion liquid is adjusted to a predetermined parameter value. Hereby, a simple possibility of optimally adapting the viscosity v to the desired operating temperature is provided. Alternatively or additionally, by suitable selection of the type and amount of the additive, a particularly exact and reproducible adjustment of the refractive index of the immersion liquid can be made.

In further advantageous development, the at least one additive includes an alkylnaphthalene, a chloronaphthalene, a bromonaphthalene, a iodonaphthalene, a phenylnaphthalene and/or a benzylnaphthalene. Therein, all of the position isomers of the mentioned additives are to be considered as co-disclosed. By alkylnaphthalene, for example, methyl-, ethyl-, n-propyl- or iso-propylnaphthalene is to be understood. However, alkylnaphthalenes with longer-chain branched and/or unbranched alkyl chains as well as multi-substituted naphthalenes can also be provided. By use of one or more of the mentioned additives, the requirements to the immersion liquid regarding dispersion, viscosity, low volatility and wettability of slides are reliably and inexpensively satisfied. Since the mentioned additives additionally each dispose of at least one ring structure and partially of refractive index increasing functional groups, it is ensured that the immersion liquid disposes of a high refractive index even with higher mass fractions of additive. The mentioned additives are additionally commercially reliably and long-ranging available and can be converted to a high optical quality with usual preparative methods (e.g. vacuum distillation) in simple and inexpensive manner.

In a further aspect, the invention relates to an immersion liquid, which includes at least one compound of the general formula III

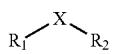
(formula III)

in which X denotes independently of each other O, S, $NR_3$ with $R_3$ selected from hydrogen or hydrocarbon,

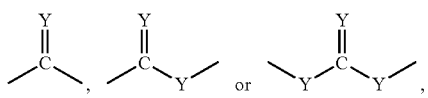

wherein Y denotes independently of each other O, S or $NR_4$ with $R_4$ selected from hydrogen or hydrocarbon. Therein, all of the enantiomers and racemic mixtures of the compound are to be considered as encompassed. The compound of the general formula III has a refractive index n of at least 1.60 at 20° C. in the wavelength range between 435 nm and 440 nm. The immersion liquid is in particular suitable for immersion objectives with high NA for microscopes, in particular near-field microscopes, and has a plurality of advantageous characteristics. Thus, the compound of the general formula III has a high refractive index n of at least 1.60, wherein a simple refractive index adaptation—for example to the used cover glass material—is allowed due to the variable chemical structure of the compound. Therefore, the optical characteristics of the immersion liquid are optimally adaptable to different operating temperatures, for example 23° C. and 37° C. Moreover, the immersion liquid has a particularly low intrinsic fluorescence F, which is below 10 mg/l quinine sulfate equivalents at an excitation wavelength of 405 nm and a fluorescence emission of 485 nm. Further advantages are in sufficient wetting of glass surfaces (cover glasses etc.) as well as a high color stability of usual microscopy dyes, since the immersion liquid does not cause decoloration of preparations in operations without cover glass. Thus, the immersion liquid is very well suited for various microscopic techniques, in particular for the fluorescence microscopy, due to its various advantages. Therein, it can basically be provided that the immersion liquid includes two or more compounds of the general formula III, thereby providing a particularly simple and precise adaptability of the optical and mechanical characteristics of the immersion liquid to different profiles of requirement.

Further advantages arise by the compound of the general formula III having a refractive index n of at least 1.52 and preferably of at least 1.57 at 20° C. in the wavelength range between 440 nm and 645 nm. Hereby, the immersion liquid has a high refractive index over a large wavelength range, whereby very different microscopic techniques can be performed with high resolution.

In a further advantageous development of the invention, it is provided that $R_1$ and/or $R_2$ of the at least one compound each include at least one ring structure. Due to the at least one ring structure, the immersion liquid is high-boiling and does not or not to an appreciable extent evaporate at the mentioned operating temperatures. Hereby, it is reliably ensured on the one hand that refractive index variations will not occur during the application, on the other hand, the immission values in the operating range are also substantially reduced.

In a further advantageous development of the invention, it is provided that $R_1$ and/or $R_2$ of the compound of the general formula III has the general formula IV

(formula IV)

wherein $R_3$ denotes at least one ring structure and Y denotes $(CR_5R_5)_n$. Therein, $R_5$ is each independently selected from hydrogen or hydrocarbon and n is an integer between 1 and 10. In this manner, the two ring structures can be spatially separated from each other by an adjustable spacer (Z), whereby, besides the optical characteristics of the compound of the general formula I, in particular the viscosity and volatility thereof are also specifically modifiable.

A further aspect of the invention relates to a compound of the general formula V

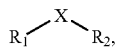
(formula V)

in which $R_1$ and $R_2$ each include at least one ring structure, X denotes: O, S, $NR_3$ with $R_3$ selected from hydrogen or hydrocarbon,

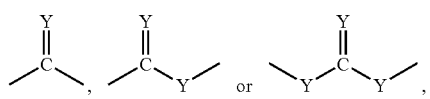

wherein Y is independently of each other O, S or $NR_4$ with $R_4$ selected from hydrogen or hydrocarbon. Therein, all of the enantiomers and racemic mixtures of the compound are to be considered as encompassed. The compound of the general formula V has a refractive index n of at least 1.60 at 20° C. in the wavelength range between 435 nm and 440 nm. The advantages arising from this are apparent from the preceding descriptions and correspondingly apply to the compound of the general formula V. Thus, the compound of the general formula V allows providing an immersion liquid, which has a refractive index as high as possible with improved suitability for the microscopy at the same time. Therein, advantageous developments of the above explained immersion liquids are to be considered as advantageous developments of the compound of the general formula V—if applicable.

A further aspect of the invention relates to a use of one of the immersion liquids and/or of a compound according to anyone of the preceding embodiments as an immersion oil for a microscope, in particular for a near-field microscope. The features and advantages thereof arising from this are apparent from the preceding descriptions and correspondingly apply to the use according to the invention.

Further features of the invention are apparent from the claims and the embodiments. The features and feature combinations mentioned above in the description as well as the features and feature combinations mentioned below in the embodiments are usable not only in the respectively specified combination, but also in other combinations or alone without departing from the scope of the invention.

PREFERRED IMPLEMENTATION OF THE INVENTION

The following examples illustrate embodiments for compounds of the general formulas I, II and III, which are usable individually or in combination with further compounds of the general formulas I, II and III as an immersion liquid for microscopes. If needed, additionally, an additive for adjusting the viscosity v and/or the refractive index n of the immersion liquid to a predetermined parameter value can be provided. Suitable additives for example include alkylnaphthalenes such as methyl-, ethyl-, n-propyl- or iso-propyl-naphthalene, as well as chloronaphthalenes, bromonaphthalenes, iodonaphthalenes, phenylnaphthalenes and/or benzylnaphthalenes.

Therein, all of the examples satisfy the following requirements:
Refractive index n>1.60 (at 20° C.)
Abbe number (dispersion) $V_e \geq 20$
Sufficient transmission in the range of 380 nm to 1000 nm
Low intrinsic fluorescence: F (405 nm/485 nm)<10 mg/l quinine sulfate equivalent
Viscosity at operating temperature >80 mm²/s
At usual operating temperature not or virtually not volatile
Sufficient wetting of glass surfaces (cover glasses etc.)
Color stable with respect to microscopy dyes such that decoloration of preparations in operations without cover glass does not occur
Long-term availability
Optimization of the optical characteristics by usual and inexpensive preparative methods (e.g. short-path vacuum distillation)

By suitable selection and/or combination of the compounds of the general formulas I, II and III as well as optionally of one or more additives, immersion liquids can be provided, which among other things have the following characteristics:
Immersion liquid adjustable to different operating temperatures, in particular 23° C. and 37° C. (in particular with respect to refractive index and viscosity)
Reproducibility of the refractive index n to ±.0005
Possibility of refractive index adaptation to the used cover glass material

EXAMPLE 1

1-Naphthylacetic acid benzyl ester

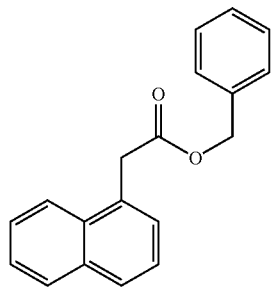 [SMILES: O=C(Cc1cccc2ccccc12)OCc1ccccc1]

Benzyl-2-(naphthalene-1-yl)acetate

Molecular weight 276 g/mol
With respect to the general formula I, therein:
X=

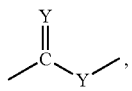

$Y=O$, $R_1=R_5-Z-$, $R_5$=naphthalinyl-, $Z=CH_2$ and $R_2$=benzyl, such that $R_1$ and $R_2$ each include at least one—presently aromatic—ring structure. 1-Naphthylacetic acid benzyl ester has the following characteristics:
Refractive indices at 20° C.:
$n_g$ (435.8 nm)=1.6476
$n_F'$ (480.0 nm)=1.6331
$n_e$ (546.1 nm)=1.6192
$n_D$ (589.3 nm)=1.6130
$n_{C'}$ (643.8 nm)=1.6072
Abbe number (dispersion): $V_e$=23.9
The Abbe number is calculated as follows:

$$V_e=(n_e-1)/(n_F'-n_{C'})$$

Viscosity (at 20° C.): 86 mm²/s

Alternatively or additionally to the shown naphthalinyl or phenyl ring structure, the compound of the general formulas I, II and III can basically include one or more ring structure elements from the non-exhaustive group of acridinyl-, adamantanyl-, anthracenyl-, azepinyl-, azulenyl-, benoxadiazinyl-, benzofuranyl-, benzopyran-onyl-, benzopyranyl-, benzothiophenyl-, benzoxazinyl-, benzyl-, biphenyl-, carbazolyl-, cinnolinyl-, coumaranyl-, diazepinyl-, dioxazolyl-, dioxinyl-, dithianyl-, fluorenyl-, furyl-, quinazolinyl-, imidazoline-2-thionyl-, imidazolyl-, indenyl-, indolinyl-, isobenzofuranyl-, isoquinolinyl-, isothiazolyl-, isoxazolyl-, morpholinyl-, naphthyl-, naphthyridinyl-, norbornanyl-, norpinanyl-, oxadiazinyl-, oxadiazolyl-, oxathiazinyl-, oxathiazolyl-, oxathiolyl-, oxatriazolyl-, oxazinyl-, oxazolonyl-, oxazolyl-, oxepinyl-, phenalenyl-, phenanthrenyl-, phenazinyl-, phenothiazinyl-, phenoxazinyl-, phenyl-, phthalazinyl-, pteridinyl-, pyranyl-, pyrazinyl-, pyrazolyl-, pyridazinyl-, pyridinyl-, pyrimidinyl-, pyronyl-, pyrrolyl-, quinolinyl-, quinolizinyl-, quinoxalinyl-, quinuclidinyl-, thiadiazolyl-, thiazolyl-, thiepinyl-, thiomorpholinyl-, thiophenyl-, thiophenyl-, triazinyl-, triazolyl-, tricyclodecanyl-, trithianyl- or xanthenyl- as the ring structure. Basically, it can also be provided that Z is a longer-chain branched or unbranched alkyl radical with 2, 3, 4, 5, 6, 7, 8, 9 or 10 carbon atoms in the alkyl chain. Furthermore, basically, it can be provided that the immersion liquid is formed free of halogen and/or heavy metal and/or without addition of elemental sulfur.

EXAMPLE 2

1-Naphthylacetic acid tricyclodecanemethylol ester

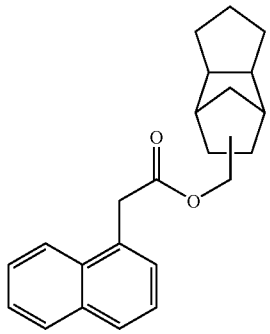

Molecular weight 334 g/mol
Refractive indices at 20° C.:
$n_g$ (435.8 nm)=1.6097
$n_{F'}$ (480.0 nm)=1.5988
$n_e$ (546.1 nm)=1.5883
$n_D$ (589.3 nm)=1.5837
$n_{C'}$ (643.8 nm)=1.5790
Abbe number (Dispersion): $V_e$=29.7
Viscosity (at 20° C.): 2180 mm$^2$/s

EXAMPLE 3

1-Naphthylacetic acid-[2-(phenylthio)-ethyl]ester

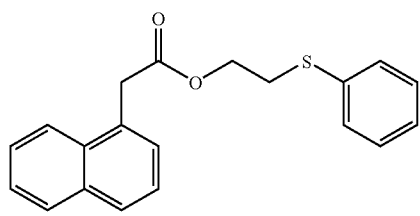 [SMILES: O=C(Cc1cccc2ccccc12)OCCSc1ccccc1]

2-(Phenylthio)ethyl-2-(naphthalene-1-yl)acetate

Molecular weight 322 g/mol
Refractive indices at 20° C.:
$n_g$ (435.8 nm)=1.6609
$n_{F'}$ (480.0 nm)=1.6466
$n_e$ (546.1 nm)=1.6327
$n_D$ (589.3 nm)=1.6262
$n_{C'}$ (643.8 nm)=1.6202
Abbe number (dispersion): $V_e$=24.0

EXAMPLE 4

1-Naphthylacetic acid-(2-methylolthienyl)ester

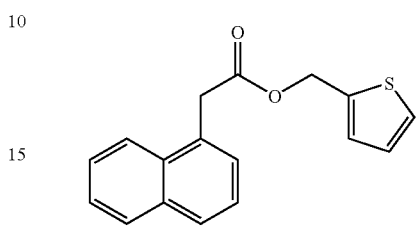

Thiophen-2-ylmethyl-2-(naphthalene-1-yl)acetate

Molecular weight 282 g/mol
Refractive indices at 20° C.:
$n_g$ (435.8 nm)=1.6618
$n_{F'}$ (480.0 nm)=1.6468
$n_e$(546.1 nm)=1.6327
$n_D$ (589.3 nm)=1.6261
$n_{C'}$ (643.8 nm)=1.6201
Abbe number (dispersion): $V_e$=23.7

EXAMPLE 5

1-Naphthylacetic acid-(2-biphenyl)ester

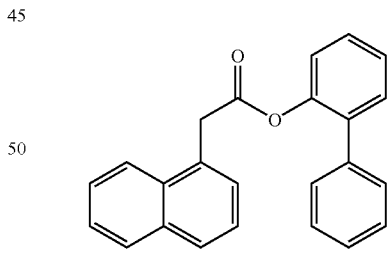

Molecular weight 338 g/mol
Refractive indices at 20° C.:
$n_g$ (435.8 nm)=1.6810
$n_{F'}$ (480.0 nm)=1.6650
$n_e$ (546.1 nm)=1.6496
$n_D$ (589.3 nm)=1.6427
$n_{C'}$ (643.8 nm)=1.6360
Abbe number (dispersion): $V_e$=22.4
1-Naphthylacetic acid-(2-biphenyl)ester is highly viscous.

EXAMPLE 6

1-Naphthylacetic acid-phenyl ester

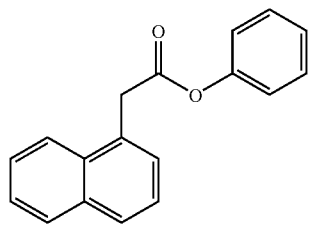 [SMILES: O=C(Cc1cccc2ccccc12)Oc1ccccc1]

Phenyl-2-(naphthalene-1-yl)acetate

Molecular weight 262 g/mol
Refractive indices at 20° C.:
$n_g$ (435.8 nm)=1.6562
$n_{F'}$ (480.0 nm)=1.6413
$n_e$ (546.1 nm)=1.6269
$n_D$ (589.3 nm)=1.6201
$n_{C'}$ (643.8 nm)=1.6141
Abbe number (dispersion): $V_e$=23.0

EXAMPLE 7

1-Naphthylacetic acid-thiophenyl ester

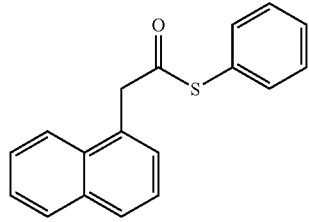 [SMILES: O=C(Cc1cccc2ccccc12)Sc1ccccc1]

S-Phenyl-2-(naphthalene-1-yl)ethanethioate

Molecular weight 278 g/mol
Refractive indices at 20° C.:
$n_g$ (435.8 nm)=1.7059
$n_{F'}$ (480.0 nm)=1.6877
$n_e$ (546.1 nm)=1.6706
$n_D$ (589.3 nm)=1.6630
$n_{C'}$ (643.8 nm)=1.6555
Abbe number (dispersion): $V_e$=20.8
Viscosity (at 20° C.): 1022 mm²/s

EXAMPLE 8

1-Naphthylacetic acid-thiobenzyl ester

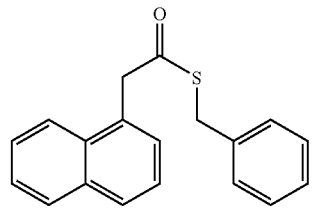 [SMILES: O=C(Cc1cccc2ccccc12)SCc1ccccc1]

S-Benzyl-2-(naphthalene-1-yl)ethanethioate

Molecular weight 292 g/mol
Refractive indices at 20° C.:
$n_g$ (435.8 nm)=1.6902
$n_{F'}$ (480.0 nm)=1.6739
$n_e$ (546.1 nm)=1.6579
$n_D$ (589.3 nm)=1.6509
$n_{C'}$ (643.8 nm)=1.6442
Abbe number (dispersion): $V_e$=22.2
Viscosity (at 20° C.): 308 mm²/s

EXAMPLE 9

Tricyclodecane-dimethanol-bis-(1-naphthylacetic acid ester)

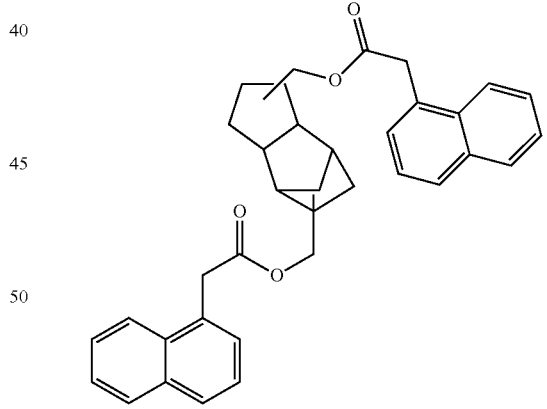

Molecular weight 532 g/mol
Refractive indices at 20° C.:
$n_g$ (435.8 nm)=1.6407
$n_{F'}$ (480.0 nm)=1.6282
$n_e$ (546.1 nm)=1.6159
$n_D$ (589.3 nm)=1.6102
$n_{C'}$ (643.8 nm)=1.6050
Abbe number (dispersion): $V_e$=26.5
Tricyclodecane-dimethanol-bis-(1-naphthylacetic acid ester) is highly viscous.

EXAMPLE 10

1-Naphthoic acid benzyl ester

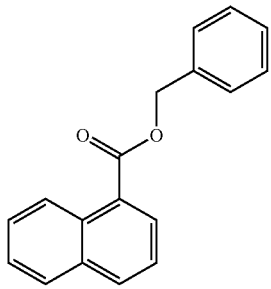 [SMILES: O=C(OCc1ccccc1)c1cccc2ccccc12]

Benzyl-1-Naphthoate

Molecular weight 262 g/mol
Refractive indices at 20° C.:
$n_g$ (435.8 nm)=1.6710
$n_{F'}$ (480.0 nm)=1.6536
$n_e$ (546.1 nm)=1.6368
$n_D$ (589.3 nm)=1.6292
$n_{C'}$ (643.8 nm)=1.6225
Abbe number (dispersion): $V_e$=20.5

EXAMPLE 11

2-Naphthoxyacetic acid benzyl ester

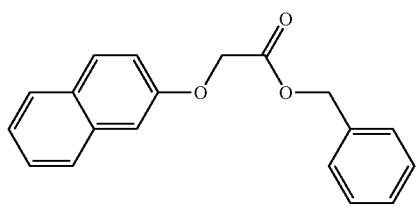 [SMILES: O=C(COc1ccc2ccccc2c1)OCc1ccccc1]

Benzyl-2-(naphthalene-2-yloxy)acetate

Molecular weight 292 g/mol
Refractive indices at 20° C.:
$n_g$ (435.8 nm)=1.6506
$n_{F'}$ (480.0 nm)=1.6359
$n_e$ (546.1 nm)=1.6219
$n_D$ (589.3 nm)=1.6158
$n_{C'}$ (643.8 nm)=1.6094
Abbe number (dispersion): $V_e$=23.5
Melting point ca. 55° C.

EXAMPLE 12

2-Thiopheneacetic acid-(1-methylolnaphthyl)ester

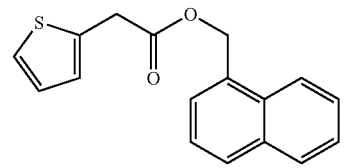 [SMILES: O=C(Cc1cccs1)OCc1cccc2ccccc12]

Naphthalene-1-ylmethyl-2-(thiophene-2-yl)acetate

Molecular weight 282 g/mol
Refractive indices at 20° C.:
$n_g$ (435.8 nm)=1.6601
$n_{F'}$ (480.0 nm)=1.6455
$n_e$ (546.1 nm)=1.6312
$n_D$ (589.3 nm)=1.6249
$r_{C'}$ (643.8 nm)=1.6186
Abbe number (dispersion): $V_e$=23.5

EXAMPLE 13

Phenylthioacetic acid benzyl ester

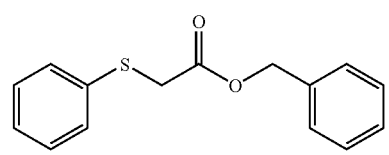 [SMILES: O=C(CSc1ccccc1)OCc1ccccc1]

Benzyl-2-(phenylthio) acetate

Molecular weight 258 g/mol
Viscosity (at 20° C.): 13 mm²/s
Refractive indices at 20° C.:
$n_g$ (435.8 nm)=1.6166
$n_{F'}$ (480.0 nm)=1.6056
$n_e$ (546.1 nm)=1.5948
$n_D$ (589.3 nm)=1.5896
$n_{C'}$ (643.8 nm)=1.5845
Abbe number (dispersion): $V_e$=28.2

EXAMPLE 14

Phenylthioacetic acid-(1-methylolnaphthyl)ester

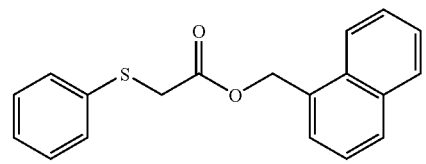 [SMILES: O=C(CSc1ccccc1)OCc1cccc2ccccc12]

Naphthalene-1-ylmethyl-2-(phenylthio)acetate

Molecular weight 308 g/mol
Refractive indices at 20° C.:

$n_g$ (435.8 nm)=1.6768
$n_{F'}$ (480.0 nm)=1.6610
$n_e$ (546.1 nm)=1.6459
$n_D$ (589.3 nm)=1.6390
$n_{C'}$ (643.8 nm)=1.6327
Abbe number (dispersion): $V_e$=22.8

EXAMPLE 15

Phenylthioacetic acid-(2-phenylthioethyl)ester

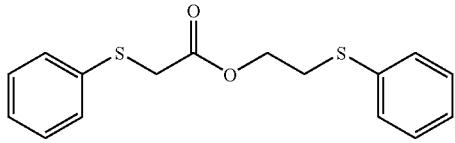 [SMILES: O=C(CSc1ccccc1)OCCSc1ccccc1]

2-(Phenylthio) ethyl-2-(phenylthio) acetate

Molecular weight 304 g/mol
Refractive indices at 20° C.:
$n_g$ (435.8 nm)=1.6387
$n_{F'}$ (480.0 nm)=1.6266
$n_e$ (546.1 nm)=1.6148
$n_D$ (589.3 nm)=1.6093
$n_{C'}$ (643.8 nm)=1.6041
Abbe number (dispersion): $V_e$=27.3

EXAMPLE 16

Phenylthioacetic acid-(biphenyl-4-methyl)ester

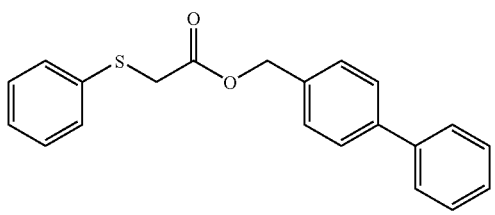 [SMILES: O=C(CSc1ccccc1)OCc1ccc(-c2ccccc2)cc1]

Molecular weight 334 g/mol
Refractive indices at 20° C.:
$n_g$ (435.8 nm)=1.6661
$n_{F'}$ (480.0 nm)=1.6515
$n_e$ (546.1 nm)=1.6369
$n_D$ (589.3 nm)=1.6301
$n_{C'}$ (643.8 nm)=1.6234
Abbe number (dispersion): $V_e$=22.7
Melting point ca. 53° C.

EXAMPLE 17

(2-Phenylthio)phenylacetic acid-(1-methylolnaphthyl)ester

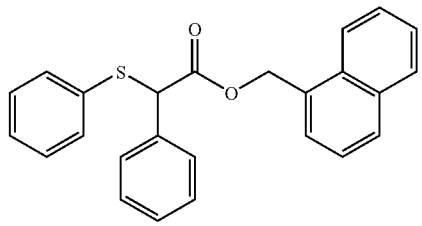 [SMILES: O=C(OCc1cccc2ccccc12)C(Sc1ccccc1)c1ccccc1]

Naphthalene-1-ylmethyl-2-phenyl-2-(phenylthio) acetate

Molecular weight 384 g/mol
Refractive indices at 20° C.:
$n_g$ (435.8 nm)=1.6851
$n_{F'}$ (480.0 nm)=1.6693
$n_e$ (546.1 nm)=1.6539
$n_D$ (589.3 nm)=1.6468
$n_{C'}$ (643.8 nm)=1.6403
Abbe number (dispersion): $V_e$=22.5
(Naphthalene-1-ylmethyl-2-phenyl-2-(phenylthio)acetate) is highly viscous.

EXAMPLE 18

For preparing an immersion liquid usable as an immersion oil for a near-field microscope according to an embodiment, 92 mol % of 1-Naphthylacetic acid-thiophenyl ester (NETPE) and 8 mol % of 1-Naphthylacetic acid-thiobenzyl ester (NETBE) are mixed. The resulting immersion liquid has the following characteristics:
Refractive indices at 20° C.:
$n_g$ (435.8 nm)=1.7041
$n_{F'}$ (480.0 nm)=1.6860
$n_e$ (546.1 nm)=1.6690
$n_D$ (589.3 nm)=1.6617
$n_{C'}$ (643.8 nm)=1.6543
Abbe number (dispersion): $V_e$=21.1

EXAMPLE 19

For preparing an immersion liquid usable as an immersion oil for a near-field microscope according to a further embodiment, 25 mol % of 1-Naphthylacetic acid-thiophenyl ester (NETPE) and 75 mol % of 1-Naphthylacetic acid-thiobenzyl ester (NETBE) are mixed. The resulting immersion liquid has the characteristics listed in table 1.

TABLE 1

| Refractive indices at 20° C. | Refractive indices at 23° C. |
| --- | --- |
| $n_g$ (435.8 nm) = 1.6937 | $n_g$ (435.8 nm) = 1.6924 |
| $n_{F'}$ (480.0 nm) = 1.6768 | $n_{F'}$ (480.0 nm) = 1.6755 |
| $n_e$ (546.1 nm) = 1.6608 | $n_e$ (546.1 nm) = 1.6596 |
| $n_D$ (589.3 nm) = 1.6536 | $n_D$ (589.3 nm) = 1.6523 |
| $n_{C'}$ (643.8 nm) = 1.6466 | $n_{C'}$ (643.8 nm) = 1.6453 |

TABLE 1-continued

| Refractive indices at 20° C. | Refractive indices at 23° C. |
|---|---|
| Viscosity (at 20° C.): 391 mm²/s | Viscosity (at 20° C.): 277 mm²/s |

Abbe number (dispersion): $V_e = 21.9$

By variation of the composition and mixing ratios of the immersion liquid it is possible to adjust a desired target refractive index to $n_e \pm 0.0005$ in reproducible manner. Thereby, it is possible to optimally match immersion liquid and optic design of the immersion objectives to each other. Additionally, there is the possibility of realizing a refractive index adaptation to the respectively used cover glass material. This presents an important requirement for example in the near-field microscopy. If one arranges in the present embodiment as the variation width 10 mol % NETPE+90 mol % NETBE to
90 mol % NETPE+10 mol % NETBE
the following refractive index ranges are possible with this mixture:
at 23° C.: $n_e$=1.658 to 1.668
at 37° C.: $n_e$=1.652 to 1.662

Suitable cover glass materials are for example:
SF 9 ($n_e$=1.65907/$V_e$=33.41); and
SF 50 ($n_e$=1.65944/$V_e$=32.63) of Schott AG (Mainz). In connection with an SF 50 cover glass, one achieves for example with the immersion liquid (IF) containing 25 mol % NETP and 75 mol % NETB the characteristics listed in table 2.

TABLE 2

| Immersion liquid IF Refractive indices 23° C. | SF 50(Schott) | Δn (IF-SF50) |
|---|---|---|
| $n_g$ (435.8 nm) = 1.6924 | 1.6806 | 0.0118 |
| $n_{F'}$ (480.0 nm) = 1.6755 | 1.6700 | 0.0055 |
| $n_e$ (546.1 nm) = 1.6596 | 1.6594 | 0.0002 |
| $n_D$ (589.3 nm) = 1.6523 | 1.6546 | −0.0023 |
| $n_{C'}$ (643.8 nm) = 1.6453 | 1.6498 | −0.0045 |

EXAMPLE 20

For preparing immersion liquids (IF) usable as an immersion oil for a near-field microscope according to a further embodiment, the following mixtures are prepared:

IF1:
98 wt.-% mixed ester of 40 mol % NETPE+60 mol % NETBE
2 wt.-% NETBE

IF2:
97.5 wt.-% mix ester of 92 mol % NETPE+8 mol % NETBE
2.5 wt.-% NEBE with:
NETPE=1-Naphthylacetic acid thiophenyl ester
NETBE=1-Naphthylacetic acid thiobenzyl ester
NEBE=1-Naphthylacetic acid benzyl ester The immersion liquids IF1 and IF2 have the characteristics listed in table 3, wherein IF1 is optimized to an operating temperature of 23° C. and IF2 is optimized to an operating temperature of 37° C.

TABLE 3

| Operating | IF1 | | IF2 | |
|---|---|---|---|---|
| temperature | 23° C. | 37° C. | 37° C. | 23° C. |
| Refractive indices n | | | | |
| $n_g$ (435.8 nm) | 1.6942 | 1.6881 | 1.6953 | 1.7015 |
| $n_{F'}$ (480.0 nm) | 1.6774 | 1.6713 | 1.6779 | 1.6840 |
| n (508.5 nm) | 1.6695 | 1.6635 | 1.6696 | 1.6757 |
| $n_e$ (546.1 nm) | 1.6610 | 1.6550 | 1.6610 | 1.6671 |
| n (578.0 nm) | 1.6555 | 1.6495 | 1.6553 | 1.6614 |
| $n_D$ (589.3 nm) | 1.6539 | 1.6479 | 1.6535 | 1.6596 |
| $n_{C'}$ (643.8 nm) | 1.6470 | 1.6410 | 1.6463 | 1.6523 |
| $(n_{F'} - n_{C'})$ | 0.0304 | 0.0303 | 0.0316 | 0.0317 |
| Dispersion $V_e$ | 21.7 | 21.6 | 20.9 | 21.0 |
| Residual fluorescence F(405 nm/ 485 nm) [quinine sulfate equivalent] | 11.0 mg/l | | | 11.5 mg/l |
| Transmission [d = 10 mm] | | | | |
| at 700 nm | 99% | | | 99% |
| at 600 nm | 99% | | | 99% |
| at 550 nm | 98% | | | 99% |
| at 500 nm | 93% | | | 93% |
| at 450 nm | 90% | | | 91% |
| at 420 nm | 76% | | | 75% |
| at 400 nm | 42% | | | 38% |
| at 390 nm | 21% | | | 18% |
| at 380 nm | 7.4% | | | 6.5% |
| at 370 nm | 1.3% | | | 1.2% |
| Viscosity [mm²/s] | 310 | | 130 | 550 |

The parameter values specified in the documents for definition of process and measurement conditions for the characterization of specific characteristics of the subject matter of the invention are to be considered as encompassed by the scope of the invention even within the scope of deviations—for example due to measurements errors, system errors, weighing errors, DIN tolerances and the like.

The invention claimed is:

1. An immersion liquid including at least one compound of the general formula I $$R_1 \diagup X \diagdown R_2,$$
(formula I)

in which:

$R_1$ and $R_2$ each include at least one ring structure; and

X denotes: O, S, or $NR_3$ with $R_3$ selected from the group consisting of hydrogen, hydrocarbon,

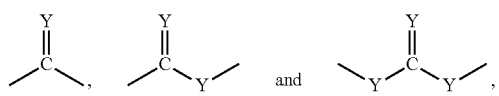

wherein Y denotes independent of each other O, S or $NR_4$ with $R_4$ selected from hydrogen or hydrocarbon.

2. The immersion liquid according to claim 1, wherein $R_1$ has the general formula II $$R_5 - Z -$$
(formula II)

wherein:

R$_5$ includes the at least one ring structure; and

Z denotes (CR$_6$R$_6$)$_n$ wherein R$_6$ is each independently selected from hydrogen or hydrocarbon and n is an integer between 1 and 10.

3. The immersion liquid according to claim 1, wherein the compound of the general formula I has a refractive index n of at least 1.52 at 20° C. in the wavelength range between 435 nm and 645 nm.

4. The immersion liquid according to claim 1, wherein the compound of the general formula I has a transmission of at least 1% in the wavelength range between 370 nm and 400 nm, a transmission of at least 15% in the wavelength range between 400 nm and 420 nm, a transmission of at least 40% in the wavelength range between 420 nm and 450 nm, and a transmission of at least 70% in the wavelength range between 450 nm and 800 nm, at 20° C. and with a layer thickness of 10 mm.

5. The immersion liquid according to claim 1, wherein the immersion liquid has a viscosity v of at least 50 mm$^2$/s in the temperature range between 20° C. and 40° C.

6. The immersion liquid according to claim 1, wherein the immersion liquid has an Abbe number V$_e$ of at least 18 in the temperature range between 20° C. and 40° C.

7. The immersion liquid according to claim 1, wherein at least one of R$_1$ and R$_2$ includes at least one ring structure selected from the group consisting of monocyclic, bicyclic and tricyclic ring structure.

8. The immersion liquid according to claim 1, wherein at least one of R$_1$ and R$_2$ includes at least one ring structure selected from the group consisting of saturated, unsaturated, aromatic ring structure, and combinations thereof.

9. The immersion liquid according claim 1, wherein at least one of R$_1$ and R$_2$ includes at least one ring structure with at least one heteroatom.

10. The immersion liquid according to claim 1, wherein at least one of R$_1$ and R$_2$ includes at least one further functional group.

11. The immersion liquid according to claim 10, in which the at least one further functional group is selected from the group consisting of carboxylic acid, thiocarboxylic acid, carboxylic acid ester, thiocarboxylic acid ester, ether, thioether, halide, ketone, thioketone, aldehyde, thioaldehyde, alcohol, thiol, amine, and combinations thereof.

12. The immersion liquid according to claim 1, further comprising at least one additive, by means of which a viscosity v and/or a refractive index n of the immersion liquid is adjusted to a predetermined parameter value.

13. The immersion liquid according to claim 12, in which the at least one additive is selected from the group consisting of alkylnaphthalene, chloronaphthalene, bromonaphthalene, iodonaphthalene, phenylnaphthalene, benzylnaphthalene, and combinations thereof.

14. The immersion liquid according to claim 1, wherein the compound of the general formula I has a refractive index n of at least 1.60 at 20° C. in the wavelength range between 435 nm and 440 nm.

15. An immersion composition for a microscope comprising the immersion liquid of claim 1 and a liquid additive.

16. The immersion liquid according to claim 3, wherein the compound of the general formula I has a refractive index n of at least 1.60 at 20° C. in the wavelength range between 435 nm and 645 nm.

17. An immersion composition for a microscope comprising the immersion liquid of claim 14 and a liquid additive.

18. The immersion liquid according to claim 1, wherein the compound of the general formula I has a transmission of at least 2% in the wavelength range between 370 nm and 400 nm, a transmission of at least 20% in the wavelength range between 400 nm and 420 nm, a transmission of at least 50% in the wavelength range between 420 nm and 450 nm, and a transmission of at least 80% in the wavelength range between 450 nm and 800 nm, at 20° C. and with a layer thickness of 10 mm.

19. The immersion liquid according claim 9, wherein the heteroatom of the at least one ring structure with at least one heteroatom is selected from the group consisting of O, N and S.

* * * * *